United States Patent
Ripin

(10) Patent No.: US 6,570,017 B2
(45) Date of Patent: May 27, 2003

(54) PREPARATION OF DIALKYLPYRIDYLBORANES

(75) Inventor: David Harold Brown Ripin, Westbrook, CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 10/226,429

(22) Filed: Aug. 23, 2002

(65) Prior Publication Data

US 2003/0083312 A1 May 1, 2003

Related U.S. Application Data

(60) Provisional application No. 60/315,183, filed on Aug. 27, 2001.

(51) Int. Cl.$^7$ ................ C07D 213/04; C07D 213/02
(52) U.S. Cl. ............................ 546/13; 546/4
(58) Field of Search ...................... 546/13, 4

(56) References Cited

PUBLICATIONS

Ishikura, M. et al.: An alternate synthesis of dialkylpyridylboranes. Heterocycles, vol. 22, pp. 2471–2474, 1984.*
Cai, W. et al.: A practical synthesis of pyridylboranes via magnesium–halogen exchange. Synlett, vol. 2, pp. 273–274, 2002.*

* cited by examiner

*Primary Examiner*—Charanjit S. Aulakh
(74) *Attorney, Agent, or Firm*—Peter C. Richardson; Paul H. Ginsburg; Adrian G. Looney

(57) ABSTRACT

The present invention relates to method for the preparation of dialkylpyridylboranes by reacting a pyridine Grignard reagent with an alkoxydialkylborane or a trialkylborane. The reaction can be conducted at a temperature ranging from about 0° C. to about 40° C. The pyridine Grignard reagent is preferably prepared in situ by the reaction of a Grignard reagent (RMgX) and a halopyridine in a suitable solvent, such as tetrahydrofuran, followed by the addition of an alkoxydialkylborane or a trialkylborane to form a dialkylpyridylborane.

15 Claims, No Drawings

PREPARATION OF DIALKYLPYRIDYLBORANES

CROSS-REFERENCE TO RELATED APPLICATION

This application claims the benefit of U.S. Provisional Patent Application No. 60/315,183, filed Aug. 27, 2001, the contents of which are hereby incorporated by reference in its entirety.

BACKGROUND OF THE INVENTION

Dialkylpyridylboranes are very useful reagents in cross-coupling reactions to prepare substituted pyridine derivatives. Substituted pyridine derivatives may be used in the synthesis of the compounds of formula (I) referred to in WO 99/57101, published Nov. 11, 1999, which are inhibitors of p38 MAP kinase inhibitors. Compounds that inhibit p38 MAP kinase are reported to be effective in inhibiting bone resorption, inflammation, and other immune and inflammation based pathologies. The present invention relates to an improved process for the preparation of dialkylpyridylboranes.

The current process for the synthesis of these materials involves the lithium-bromine exchange on the bromopyridine followed by trapping of the lithiopyridine with diethylmethoxyborane or triethylborane. This type of process is referred to in the following references (a) Ishikura, M.; Mano, T.; Oda, I.; Terashima, M. *Heterocycles* 1984, 22, 2471–2474; (b) Ishikura, M.; Ohta, T.; Terashima, M. *Chem. Pharm. Bull.* 1983, 31, 4573–4577; (c) Morris, G. A.; Nguyen, S. T. *Tetrahedron Lett.* 2001, 42, 2093–2096; (d) Labadie, S. S.; Rotstein, D. M.; Sjogren, E. B.; Talamas, F. X., PCT International Application No. WO 99/57101 and is illustrated in the following scheme.

Scheme 1

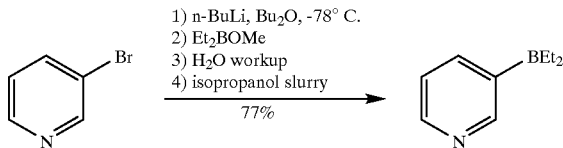

1) n-BuLi, Bu₂O, -78° C.
2) Et₃BOMe
3) H₂O workup
4) isopropanol slurry

77%

The above reaction must be run at low temperature (<−40° C. in ether or <−100° C. in tetrahydrofuran ("THF")) in order to prevent the anion from migrating, elimination of the bromide to form pyridynes, deprotonation, migration of the halide, and addition of the alkyllithium to the pyridine during the metal-halogen exchange (see, (a) Gilman, H.; Spatz, S. M. *J. Org. Chem.* 1951, 16, 1485–1494; (b) Mallet, M.; Branger, G.; Marsaia, F.; Quenguiner, G. *J. Organomet. Chem.* 1990, 382, 319–332). The required use of low temperature for this reaction adds to the cost and difficulty of producing large quantities of these materials in an industrial setting. Accordingly, it is desirable to have a method of preparing dialkylpyridylboranes without the use of low temperatures for their commercial production.

SUMMARY OF THE INVENTION

The present invention relates to a method for the preparation of dialkylpyridylboranes comprising reacting a pyridine Grignard reagent and an alkoxydialkylborane or a trialkylborane. The reaction may be performed at a temperature from about 0° C. to about 40° C.

In one preferred embodiment the invention relates to a method for the preparation of a compound of formula 2:

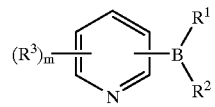

wherein $R^1$ and $R^2$ are each independently $C_1$–$C_{10}$ alkyl; $R^3$ is H, halo, $C_1$–$C_{10}$ alkyl, $C_2$–$C_{10}$ alkenyl, $C_2$–$C_{10}$ alkynyl, —C(O)($C_1$–$C_{10}$ alkyl), —(CH$_2$)$_t$($C_6$–$C_{10}$ aryl), —(CH$_2$)$_t$(4–10 membered heterocyclic), —C(O)(CH$_2$)$_t$($C_6$–$C_{10}$ aryl), or —C(O)(CH$_2$)$_t$(5–10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said $R^3$ aryl and heterocyclic groups are optionally fused to a $C_6$–$C_{10}$ aryl group, a $C_5$–$C_8$ saturated cyclic group, or a 5–10 membered heterocyclic group; 1 or 2 carbon atoms in the foregoing heterocyclic moieties are optionally substituted by an oxo (=O) moiety; the —(CH$_2$)$_t$— moieties of the foregoing $R^3$ groups optionally include a carbon-carbon double or triple bond where t is an integer from 2 to 5 and wherein m is 0–4; and the foregoing $R^3$ groups, except H, are optionally substituted by 1 to 3 $R^4$ groups; $R^4$ is $C_1$–$C_{10}$ alkyl or $C_1$–$C_{10}$ alkoxy and $R^6$ is H or $C_1$–$C_{10}$ alkyl, comprising reaction a compound of formula 1,

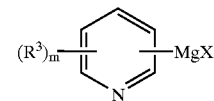

wherein $R^3$ and m are defined for formula 2 above and X is a halo with a compound of the formula $R^5BR^1R^2$, wherein $R^1$ and $R^2$ are as defined above for formula 2 and wherein $R^5$ is $C_1$–$C_{10}$ alkyl or $C_1$–$C_{10}$ alkoxy.

In one preferred embodiment $R^1$ and $R^2$ are each independently $C_1$–$C_5$ alkyl. In another preferred embodiment $R^1$ and $R^2$ are each independently $C_1$–$C_3$ alkyl. In a more preferred embodiment $R^1$ and $R^2$ are each independently methyl or ethyl.

In a preferred embodiment of the present invention $R^3$ is H, $C_1$–$C_{10}$ alkyl, $C_2$–$C_{10}$ alkenyl, $C_2$–$C_{10}$ alkynyl, —C(O)($C_1$–$C_{10}$ alkyl), —(CH$_2$)$_t$($C_6$–$C_{10}$ aryl), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said $R^3$ aryl group is optionally fused to a $C_6$–$C_{10}$ aryl group, a $C_5$–$C_8$ saturated cyclic group, or a 5–10 membered heterocyclic group; the —(CH$_2$)$_t$— moieties of the foregoing $R^1$ groups optionally include a carbon-carbon double or triple bond where t is an integer from 2 to 5; and the foregoing $R^3$ groups, except H, are optionally substituted by 1 to 3 $R^4$ groups; and wherein $R^4$ is $C_1$–$C_{10}$ alkyl or $C_1$–$C_{10}$ alkoxy.

In a preferred embodiment of the present invention X is Cl, Br, or I. In a more preferred embodiment X is Br.

The term "halo", as used herein, unless otherwise indicated, includes fluoro, chloro, bromo or iodo. Preferred halo groups are chloro, bromo, and iodo.

The term "alkyl", as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl", as used herein, unless otherwise indicated, includes monovalent hydrocarbon radicals having at least one carbon-carbon double bond and also having straight, cyclic or branched moieties as provided above in the definition of "alkyl".

The term "alkynyl", as used herein, unless otherwise indicated, includes monovalent hydrocarbon radicals having at least one carbon-carbon triple bond and also having straight, cyclic or branched moieties as provided above in the definition of "alkyl".

The term "alkoxy", as used herein, unless otherwise indicated, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The present invention relates to a method for preparing a dialkylpyridylborane comprising reacting a pyridine Grignard reagent with an alkoxydialkylborane reagent or a trialkylborane reagent. The pyridine Grignard reagent is prepared by reacting an alkylmagnesium halide or arylmagnesium halide with a halopyridine reagent. Preferably, the pyridine Grignard reagent is prepared in situ. In another preferred embodiment of the present invention the pyridine Grignard reagent is prepared by reacting a halopyridine, Mg(0), and alkyl halide or aryl halide.

In a preferred embodiment the pyridine Grignard reagent is pyridylmagnesium chloride or pyridylmagnesium bromide.

In one embodiment of the present invention the alkylmagnesium halide is $C_1$–$C_{10}$alkylmagnesium halide. In one preferred embodiment the alkylmagnesium halide is $C_1$–$C_5$alkylmagnesium halide. In one more preferred embodiment the alkylmagnesium halide is selected from the group consisting of methylmagnesium chloride, ethylmagnesium chloride, isopropylmagnesium chloride, methylmagnesium bromide, ethylmagnesium bromide, and isopropylmagnesium bromide.

In one preferred embodiment of the present invention the halopyridine reagent is chloropyridine, bromopyridine, or iodopyridine. In one more preferred embodiment the halopyridine is 3-bromopyridine.

In one embodiment of the present invention the alkoxydialkylborane is $C_1$–$C_{10}$alkoxydi($C_1$–$C_{10}$alkyl)borane. More preferably, the alkoxydialkylborane is $C_1C_{10}$alkoxydi($C_1$–$C_5$alkyl)borane. Most preferably, the alkoxydialkylborane is $C_1$–$C_{10}$alkoxydi($C_1$–$C_2$alkyl)borane. In one preferred embodiment of the present invention the $C_1$–$C_{10}$ alkoxydialkylborane is $C_1$–$C_{10}$ alkoxydimethylborane or $C_1$–$C_{10}$alkoxydiethylborane.

In another embodiment of the present invention the alkoxydialkylborane is $C_1$–$C_5$alkoxydi($C_1$–$C_{10}$alkyl)borane. In a more preferred embodiment the alkoxydialkylborane is $C_1$–$C_3$alkoxydi($C_1$–$C_5$alkyl)borane. In one embodiment of the present invention the alkoxydialkylborane is methoxydi($C_1$–$C_5$alkyl)borane or ethoxydi($C_1$–$C_5$alkyl)borane.

In one embodiment of the present invention the alkoxydialkylborane is methoxydiethylborane.

The reaction between said alkoxydialkylborane reagent or said trialkylborane reagent and said Grignard pyridine reagent is performed at temperature from about 0° C. to about 40° C. In one preferred embodiment the reaction is performed at temperature from about 10° C. to about 25° C.

DETAILED DESCRIPTION OF THE INVENTION

The present invention relates to a method to prepare dialkylpyridylboranes by the reaction a pyridine Grignard reagent and an alkoxydialkylborane or a trialkylborane at a temperature of about 0° C. to about 40° C. In one preferred embodiment the dialkylpyridylborane is prepared by the reacting an alkylmagnesium halide or an arylmagnesium halide with a halopyridine followed by the addition of a trialkylborane or alkoxydialkylborane.

Functional pyridines are prepared using a halide-lithium exchange reaction, which has to be performed at low temperatures from −100° C. to −40° C. depending on the solvent employed. The low temperature prevents side reactions such as deprotonation, elimination of lithium bromide or other reactions from occurring during the halide-metal exchange. If functional pyridines are desired in industrial environment it is often costly and inconvenient to run reactions at low temperatures. It is known in the art that the corresponding Grignard reagents are kinetically stable up to much higher temperatures (>25° C.). However, magnesiopyridines are notoriously difficult to generate directly from the corresponding pyridine halide and magnesium (0) ((a) Harris, S. A. *Iowa State Coll. J. Sci.* 1932, 6, 425; (b) Overhoff, J.; Proost, W. *Rec. Trav. Chim.* 1938, 57, 179–184; (c) Proost, W.; Wibaut, J. P. *Rec. Trav. Chim.* 1940, 59, 971; (d) Lai, Y-H. *Synthesis* 1981, 585–604; and (e) Nakane, M.; Hutchinson, C. R. *J. Org. Chem.* 1978, 43, 3922–3931).

The use of magnesium-halogen exchange reactions to generate heteroaryl Grignard reagents from the heteroaryl halide and an alkyl or aryl magnesium halide is well known.

((a) Abarbri, M.; Thibonnet, J.; Berillon, L.; Dehmel, F.; Rottlaender, M.; Knochel, P. *J. Org. Chem.* 2000, 65, 4618–4634; (b) Rottlander, M.; Boymond, L.; Berillon, L.; Lepretre, A.; Varchi, G.; Avolio, S.; Laaziri, H.; Queguiner, G.; Ricci, A; Cahiez, G.; Knochel, P. *Chem Eur. J.* 2000, 6, 767–770; (c) Lepretre, A.; Turck, A.; Ple, N.; Knochel, P.; Queguiner, G. *Tetrahedron* 2000, 56, 265–273; (d) Shimura, A.; Momotake, A.; Togo, H.; Yokoyama, M. *Synthesis* 1999, 495–499; (e) Kondo, Y.; Yoshida, A.; Sato, S.; Sakamoto, T *Heterocycles* 1996, 42, 105–108; (f) Turner, R. M.; Lindell, S. D.; Ley, S. V. *J. Org. Chem.* 1991, 56, 5739–5740; (g) Abarbri, M.; Dehmel, F.; Knochel, P. *Tetrahedron Lett.* 1999, 40, 7449–7453; (h) Dehmel, F.; Abarbri, M.; Knochel, P. *Synlett.* 2000, 345–346; and (i) Felding, J.; Kristensen, J.; Bjerregaard, T.; Sander, L.; Vedso, P.; Begtrup, M. *J. Org. Chem.* 1999, 64, 4196–4198). Pyridyl Grignard reagents have also been generated by ligand exchange reactions of aryl pyridyl sulfoxides with Grignard reagents (Shibutani, T.; Fujihara, H.; Furukawa, N. *Heteroat. Chem.* 1991, 2, 521–531). The heteroaryl Grignard may also be directly generated from the pyridyl halide, magnesium(0), and a reactive alkylhalide such as ethylbromide (Entrainment Method). The formation of pyridyl Grignard reagents via direct reaction with stoichiometric quantities of alkyl or aryl Grignard reagents is well known in the art ((a) Paradies, H. H.; Gorbing, M. *Angew. Chem. Int. Ed.* 1969, 8, 279; (b) Martin, G. J.; Mechin, B.; Leroux, Y.; Paulmier, C.; Meunier, J. C. *J. Organomet. Chem.* 1974, 67, 327–339; (c) Furukawa, N.; Shibutani, T.; Fujihara, H. *Tetrahedron Lett.* 1987, 28, 5845–5848; (d) Trecourt, F.; Breton, G.; Bonnet, V.; Mongin, F.; Marsais, F.; Queguiner, G. *Tetrahedron Lett.* 1999, 40, 4339–4342; (e) Berillon, L.; Lepretre, A.; Turck, A.; Ple, N.; Queguiner, G.; Cahiez, G.; Knochel, P. *Synlett.* 1998, 1359–1360; and (f) Trecourt, F.; Breton, G.; Bonnet, V.; Mongin, F.; Marsais, F.; Queguiner, G. *Tetrahedron* 2000, 56, 1349–1360). This process can be run within a wide temperature range as high as 40° C. and generates the halomagnesiopyridine under mild reaction conditions. The halomagnesiopyridine can be converted to the corresponding dialkylpyridylborane by reaction with a dialkylalkoxyborane or a trialkylborane at a temperature of about 0° C. to about 40° C. This reaction produces the desired dialkylpyridylborane in comparable yield and quality to that made by the reaction of the corresponding lithiated pyridine at low temperature.

The method of the present invention may be employed in the synthesis of compounds which require a pyridine substitutent. For example, the pyrazole p38 MAP kinase inhibitors of WO 99/57101 formula (I) shown below:

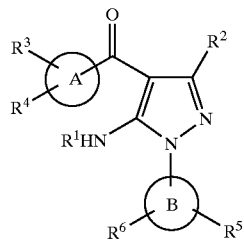

wherein A, B, $R^1$, $R^2$, $R^3$, $R^4$, $R^5$, and $R^6$ are as defined in WO 99/57101, which is hereby incorporated by reference in its entirety, may include the presence of a pyridine substituent. Accordingly, the method of the present invention can be employed to introduce the pyridine in Example 23 (5-Amino-1-(2,4-dimethylphenyl)-4-]3-(pyridin-3-yl) benzoyl]pyrazole HCl salt), shown below, of WO 99/57101, rather than the exemplified method of introducing the pyridine substituent using the traditional reagent n-butyl lithium,

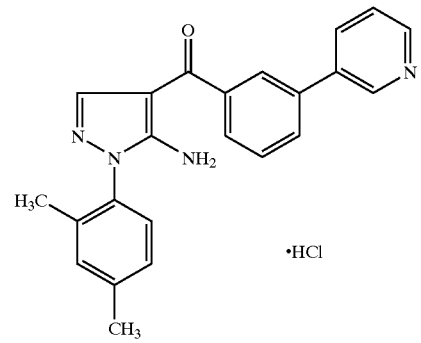

The compounds of formula (I) and their pharmaceutically acceptable salts and solvates (hereinafter referred to, collectively, as "the therapeutic compounds") can be administered orally, transdermally (e.g., through the use of a patch), parenterally or topically. Oral administration is preferred. In general, compounds of the formula (I) and their pharmaceutically acceptable salts and solvates are most desirably administered in dosages ranging from about 1.0 mg up to about 500 mg per day, preferably from about 1 to about 100 mg per day in single or divided (i.e., multiple) doses. The therapeutic compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by any of the routes previously indicated, and such administration may be carried out in single or multiple doses. More particularly, the therapeutic compounds can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The compounds of formula (I) exhibit activity as p38 MAP kinase inhibitors and are useful in the treatment of diseases mediated by cykokines, such as inhibition of bone resorption, inflammation, and other immune and inflammation-based pathologies. The activity of the compounds of formula (I) as p38 MAP kinase inhibitors can be determined using the assays described in WO 99/57101.

The following Examples are provided to illustrate aspects of the subject invention. They are not intended, nor should they be construed, to limit the invention as more fully described herein and set forth in the claims.

EXAMPLE 1

Diethyl-3-pyridylborane

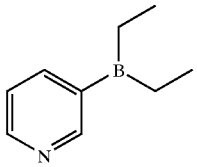

To a 2M solution of isopropyl magnesium chloride in tetrahydrofuran (200 mL, 0.4 mol) at 0° C. under nitrogen was added 3-bromopyridine (34.5 mL, 0.36 mol) over 45 min., keeping the temperature of the reaction mixture during the addition between 10° C.–25° C. The mixture was stirred for an additional hour at 0° C. after the addition. Diethyl-methoxyborane (52.6 mL, 0.4 mol) was added drop-wise between 10° C.–25° C. (cooled with ice bath) over 30 min. The reaction mixture was then stirred at 0° C. for 1 hour and then the reaction was allowed to warm to room temperature overnight. The reaction was quenched by 2N HCl (200 mL) at 0° C. The pH of the aqueous layer was adjusted to 7 using sodium carbonate, and the mixture was extracted with ethyl acetate (3×150 mL), washed with brine (150 mL), dried over sodium sulfate, and concentrated in vacuo. The crude material was slurried in isopropanol and filtered, providing the product as a white solid (41.5 g, 0.282 mol) in 78% yield. The NMR spectrum and melting point recorded for the prepared material was identical to that the NMR spectrum and melting point for diethyl-3-pyridylborane purchased from Aldrich Chemical Company, Millwaukee, Wis.

$^1$H NMR (CDCl$_3$) δ8.0 (d, J=5 Hz, 1 H), 7.7 (d, J=6 Hz, 1 H), 7.5 (s, 1 H), 7.2 (dd, J=1.9, 8 Hz, 1 H), 0.6 (m, 2 H), 0.4 (m, 6 H). $^{13}$C NMR (CDCl$_3$) δ149.3, 144.0, 141.1, 123.6, 14.6, 9.3. mp 172.0° C.–175.5° C.

EXAMPLE 2

(5-Bromo-3-pyridyl)diethylborane

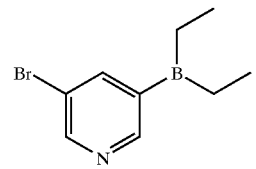

(5-Bromo-3-pyridyl)diethylborane was prepared according to the method described in Example 1 except that 3,5-dibromopyridine was used in place of 3-bromopyridine. The reaction resulted in a recovered yield of 66%.

$^1$H NMR (CDCl$_3$): 8.1 (s, 1 H), 7.9 (s, 1 H), 7.4 (s, 1 H), 0.6 (m, 4 H), 0.4 (m, 6 H). $^{13}$C NMR (CDCl$_3$): 147.4, 146.8, 142.5, 121.2, 14.6, 9.2. MS: 228.2 (M+1).

EXAMPLE 3

Diethyl-4-pyridylborane

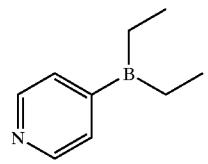

Diethyl-4-pyridylborane was prepared according to the method described in Example 1 except that 4-bromopyridine was used in place of 3-bromopyridine. The reaction resulted in a recovered yield of 88%.

$^1$H NMR (CDCl$_3$): 8.00 (d, J=5.8 Hz, 2 H), 7.25 (d, J=5.4 Hz, 2 H), 0.73 (m, 4 H), 0.52 (m, 6 H). $^{13}$C NMR (CDCl$_3$): 142.5, 129.2, 17.5, 9.5.

What is claimed is:

1. A method for preparing a dialkylpyridylborane comprising reacting a pyridine Grignard reagent with a borane reagent selected from an alkoxydialkylborane reagent and a trialkylborane reagent.

2. The method of claim 1, wherein the pyridine Grignard reagent is prepared by reacting an alkyl magnesium halide or aryl magnesium halide with a halopyridine reagent.

3. The method of claim 1 or 2, wherein the borane reagent is a $C_1$–$C_{10}$alkoxydi($C_1$–$C_{10}$alkyl)borane.

4. The method of any of claims 1, 2 and 3, wherein the borane reagent is a $C_1$–$C_5$alkoxydi($C_1$–$C_{10}$alkyl)borane.

5. The method of any of claims 1 to 4, wherein the borane reagent is methoxydiethylborane.

6. The method of any of claims 1 to 5, wherein the reaction between said borane reagent and said pyridine Grignard reagent is performed at temperature from about 0° C. to about 40° C.

7. The method of any of claims 1 to 6, wherein the reaction is performed at temperature from about 0° C.

8. The method of any of claims 1 to 7, wherein said pyridine Grignard reagent is prepared by reacting a halopyridine, Mg(0), and an alkyl halide or aryl halide.

9. The method of any of claims 1 to 8, wherein the pyridine Grignard reagent is pyridylmagnesium chloride.

10. A method for preparing a dialkylpyridylborane comprising reacting an alkyl magnesium halide or aryl magnesium halide with a halopyridine followed by the addition of an alkoxydialkylborane or trialkylborane.

11. The method of claim 10, wherein the alkyl magnesium halide is a $C_1$–$C_{10}$ alkyl magnesium halide.

12. The method of claim 10, wherein the aryl magnesium halide is a $C_6$–$C_{10}$ aryl magnesium halide.

13. The method of any of claims 10 to 12, wherein the halopyridine is chloropyridine, bromopyridine, or iodopyridine.

14. The method of any of claims 10 to 13, wherein the alkoxydialkylborane or trialkylborane is a $C_1$–$C_{10}$ alkoxydi($C_1$–$C_{10}$ alkyl)borane.

15. A method for preparing a compound of formula 2:

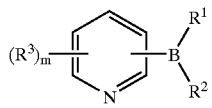

2 wherein $R^1$ and $R^2$ are each independently $C_1$–$C_{10}$ alkyl and $R^3$ is H, halo, $C_1$–$C_{10}$ alkyl, $C_2$–$C_{10}$ alkenyl, $C_2$–$C_{10}$ alkynyl, —C(O)($C_1$–$C_{10}$ alkyl), —(CH$_2$)$_t$($C_6$–$C_{10}$ aryl), —(CH$_2$)$_t$(4–10 membered heterocyclic), —C(O)(CH$_2$)$_t$($C_6$–$C_{10}$ aryl), or —C(O)(CH$_2$)$_t$(5–10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said $R^3$ aryl and heterocyclic groups are optionally fused to a $C_6$–$C_{10}$ aryl group, a $C_5$–$C_8$ saturated cyclic group, or a 5–10 membered heterocyclic group; 1 or 2 carbon atoms in the foregoing heterocyclic moieties are optionally substituted by an oxo (=O) moiety; the —(CH$_2$)$_t$— moieties of the foregoing $R^3$ groups optionally include a carbon-carbon double or triple bond where t is an integer from 2 to 5; and the foregoing $R^3$ groups, except H, are optionally substituted by 1 to 3 $R^4$ groups; $R^4$ is $C_1$–$C_{10}$ alkyl or $C_1$–$C_{10}$ alkoxy; $R^6$ is H or $C_1$–$C_{10}$ alkyl and wherein m is 0 to 4; comprising reacting a compound of formula 1,

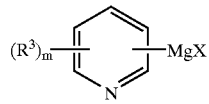

1 wherein $R^3$ and m are as defined for formula 2 above and X is a halo with a compound of the formula $R^5BR^1R^2$, wherein $R^1$, $R^2$ are as defined above for formula 2 and wherein $R^5$ is $C_1$–$C_{10}$ alkyl or $C_1$–$C_{10}$ alkoxy.

* * * * *